United States Patent [19]
Hoffmann et al.

[11] Patent Number: 5,619,041
[45] Date of Patent: Apr. 8, 1997

[54] ATOMIC ABSORPTION SPECTROMETER FOR MEASURING THE MERCURY CONCENTRATION IN A SAMPLE

[75] Inventors: Erwin Hoffmann, Hohen Neuendorf; Christian Lüdke, Berlin, both of Germany

[73] Assignee: Bodenseewerk Perkin-Elmer GmbH, Überlingen, Germany

[21] Appl. No.: 521,004

[22] Filed: Aug. 30, 1995

Related U.S. Application Data

[63] Continuation of Ser. No. 252,129, Jun. 1, 1994, abandoned.

[51] Int. Cl.⁶ .................................................. G01N 21/33
[52] U.S. Cl. ................................................. 250/373
[58] Field of Search ........................... 250/373, 339.13

[56] References Cited

U.S. PATENT DOCUMENTS

| | | | |
|---|---|---|---|
| 3,173,016 | 3/1965 | Williston et al. | 250/373 |
| 3,845,309 | 10/1974 | Helm et al. | 250/373 |
| 3,920,334 | 11/1975 | Steichen et al. | 250/373 |
| 3,932,754 | 1/1976 | Reidl et al. | 250/343 |
| 4,192,996 | 3/1980 | Kronick et al. | 250/373 |
| 5,045,704 | 9/1991 | Coates | 250/372 |
| 5,170,057 | 12/1992 | Danielson | 250/373 |

FOREIGN PATENT DOCUMENTS 291156  6/1991  Germany ................................ 250/373

OTHER PUBLICATIONS

"Non-Flame Atomic Absorption In The Vacuum Ultraviolet Region" (J.W. Robinson, P.J. Slevin, G.D. Hindman, D.K. Wolcott, Anal. Chem. Acta 61, 431, 1972.)

"New Mercury Spectrometer For The Measurement of Mercury Vapour In Air" (E. Hoffmann, Ch. Ludke, Fresenius Z. Anal. Chem. 298, 9–11, 1979).

"Improvements In The Atomic-fluorescence Determination of Mercury by The Cold-vapour Technique". (K.C. Thompson, R. G. Godden, Analyst 100, 544–548, 1975).

*Primary Examiner*—Carolyn E. Fields
*Attorney, Agent, or Firm*—Edwin T. Grimes; David Aker

[57] ABSTRACT

An atomic absorption spectrometer for measuring mercury concentration in a sample which includes an arrangement for producing emission lines of 184.9 and 253.7 nm at the same time, a sample accommodating chamber which can be irradiated with radiation of the emission lines, two electro-optical transducers responsive, with different sensitivities, to the radiation emission lines and arranged so that radiation passing through the sample chamber simultaneously impinges thereon, each extinction measuring means having a preselected extinction value range, and a comparator for switching between respective measurement ranges to determine the mercury concentration.

12 Claims, 3 Drawing Sheets

ATOMIC ABSORPTION SPECTROMETER FOR MEASURING THE MERCURY CONCENTRATION IN A SAMPLE

This is a continuation of application Ser. No. 08/252,129 filed Jun. 1, 1994, now abandoned.

The present invention relates to an atomic absorption spectrometer for measuring the mercury concentrations in a sample, with the spectrometer comprising a means for producing predetermined emission lines of the mercury, a sample accommodating chamber that can be irradiated with light of the emission lines, and means for measuring the extinction of the radiation passing through the sample accommodating chamber.

It is known that atomic absorption spectrometry is employed for mercury analysis. The Hg atom has two suitable lines which end at the ground state of the atom, but greatly differ in their detection sensitivity. (J. W. Robinson, P. J. Slevin, G. D. Hindman, D. K. Wolcott, Anal. Chem. Acta 61, 431, 1972).

Furthermore, mercury spectrometers for each of the suitable wavelengths are already known, with a grating, prism or a selective photocell being used for narrowing the spectrum of the Hg low-pressure discharge lamp which is employed as a background radiator. (E. Hoffmann, Ch. L üdke, Fresenius Z. Anal. Chem. 298, 9–11, 1979).

A disadvantage of the known assemblies is that only a limited concentration range with a high detection sensitivity can be covered because of deviation from the proportionality between measurement signal and mercury concentration. An extension of the concentration range has so far only been possible by way of relatively cumbersome enrichment or dilution methods or by the use of two devices with different concentration measuring ranges.

Furthermore, it is known that fluorescence radiation on line 253.7 nm is also used for the determination of mercury. It is marked by a high detection strength and a great concentration determination range. (K. C. Thompson, R. G. Godden Analyst 100, 544–548, 1975). The disadvantage of this arrangement is, however, that the determination of the concentration of mercury may be disturbed by fluorescence-extinguishing processes. Another disadvantage is that the fluorescence intensity is small in relation with the primary radiation. This requires a high sensitivity of the receiver and additional assemblies for keeping superimposition of the fluorescent light by scattered primary radiation small.

It is also known that the arrangement for the flow-injection method is coupled with an arrangement for the determination of mercury according to the atomic absorption method on line 253.7 nm. A disadvantage of this assembly is, however, that the detection sensitivity and the determinable concentration range do not satisfy many requirements. Another disadvantage is that special means which serve wavelength selection have to be used in this assembly.

It is now the object of the present invention to determine mercury with a high detection sensitivity within a large concentration range in a reliable manner and with a simple inexpensive assembly.

Starting from an atomic absorption spectrometer of the above-mentioned type, this object is attained according to the invention by the measures that a means is provided for simultaneously producing the emission lines 184.9 and 253.7 nm, and that two means are provided for measuring the extinction, the means having electro-optical transducers which are each responsive with different sensitivity to radiation of the emission line 184.9 and 253.7 nm, respectively, and are arranged such that radiation passing through the sample accommodating chamber simultaneously impinges on the two electro-optical transducers, and that only the extinction measurement values that fall within the extinction value ranges respectively assigned to the two extinction measuring means serve to determine the mercury concentration.

This leads to the considerable advantage that the measurement range is considerably enlarged in a measuring device. This is especially of great importance if only one sample is available for measurement, which sample would be forfeited if a measurement was performed in a device with an inappropriate measurement range.

A CsTe photocathode which is substantially responsive to radiation of the emission line 253.7 and a CsI photocathode which is substantially responsive to radiation of the emission line 184.9 are preferably provided as electro-optical transducers.

Furthermore, the provision of a beam splitter between the sample accommodating chamber and the electro-optical transducers has turned out to be expedient.

The beam splitter preferably consists of a quartz plate. It has surprisingly been found that a quartz plate can be used as a beam splitter for said application and that, when a beam splitter is used, adequate light intensities are nevertheless available for achieving a sufficient measuring accuracy.

The quartz plate has a suitable thickness (e.g. 1 mm).

Other preferred embodiments will become apparent from the subclaims.

The invention shall now be explained in the following with reference to preferred embodiments shown in the drawing, in which.

Figure 3:
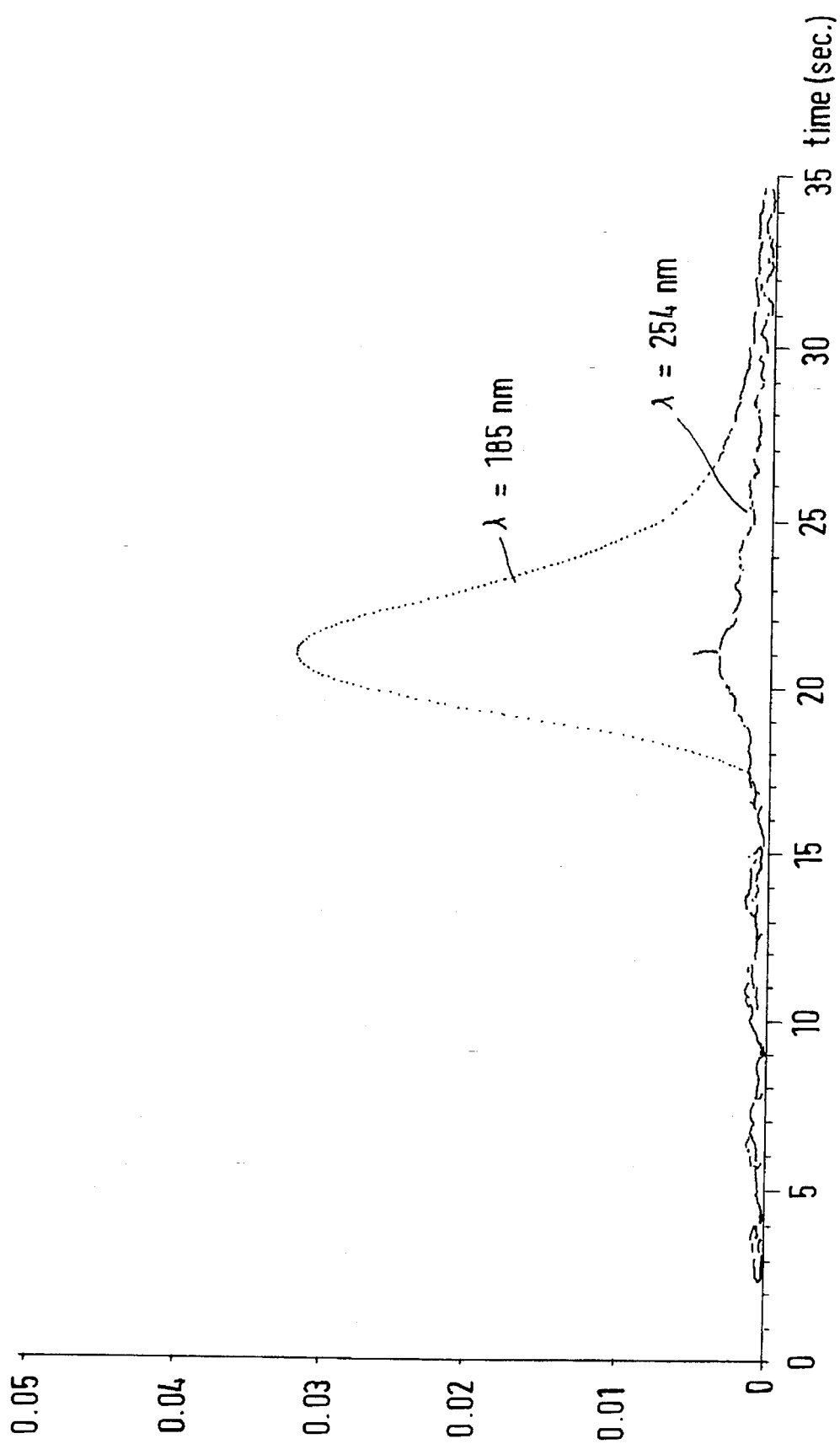
Figure 4:
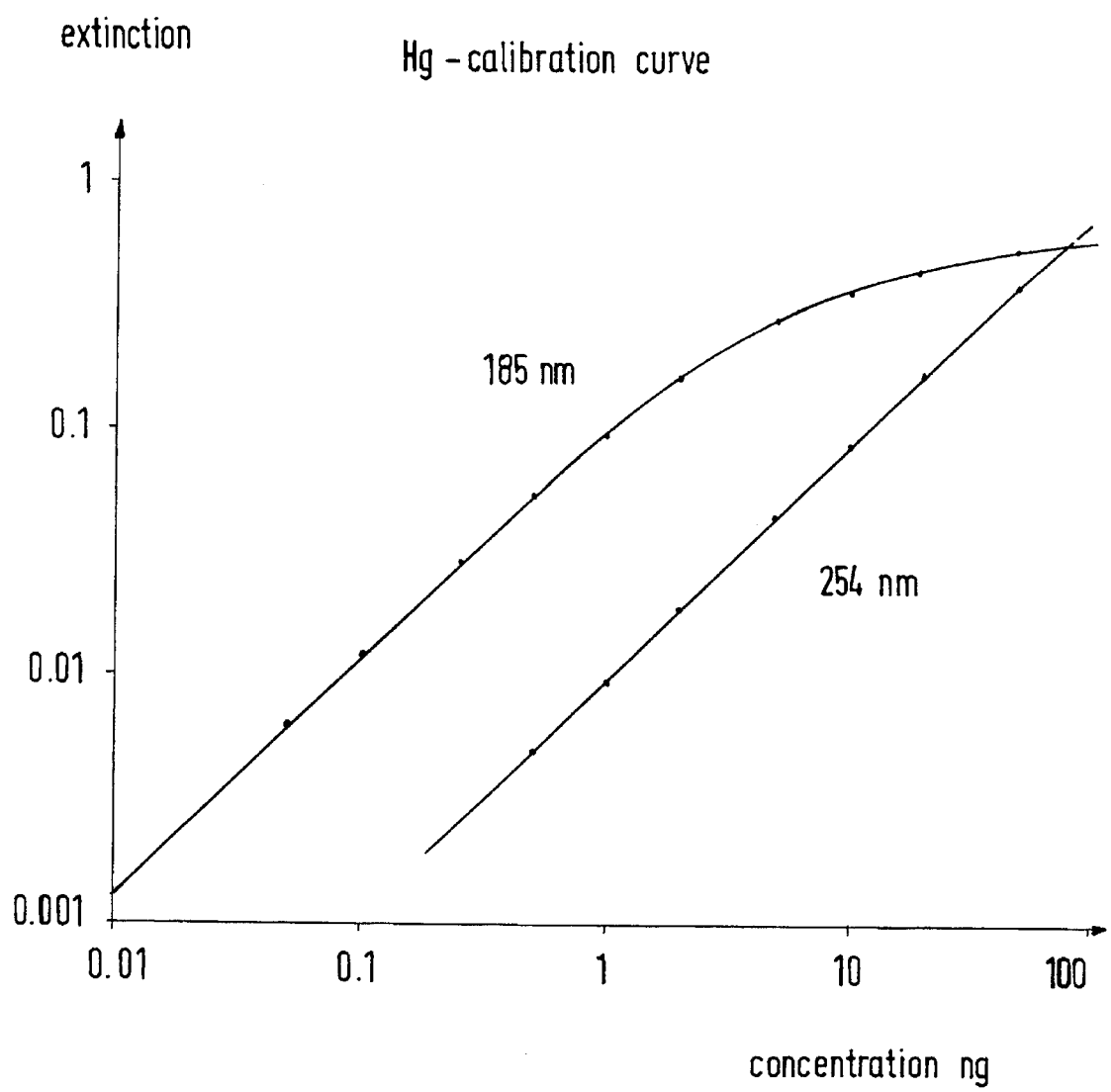

FIG. 3 shows the course of the measurement curves of the measured extinction in response to the time for a first electro-optical transducer which is preferably responsive to radiation of the wavelength 185 nm and for a second phototransducer which is preferably responsive to radiation of the wavelength 254 nm; and FIG. 4 shows two mercury calibration curves by which a respectively measured extinction is assigned to a specific mercury concentration in ng for the first optical transducer that is preferably responsive to radiation of the wavelength 185 nm, and a second electro-optical transducer that is preferably responsive to radiation of the wavelength 254 nm.

Figure 1:
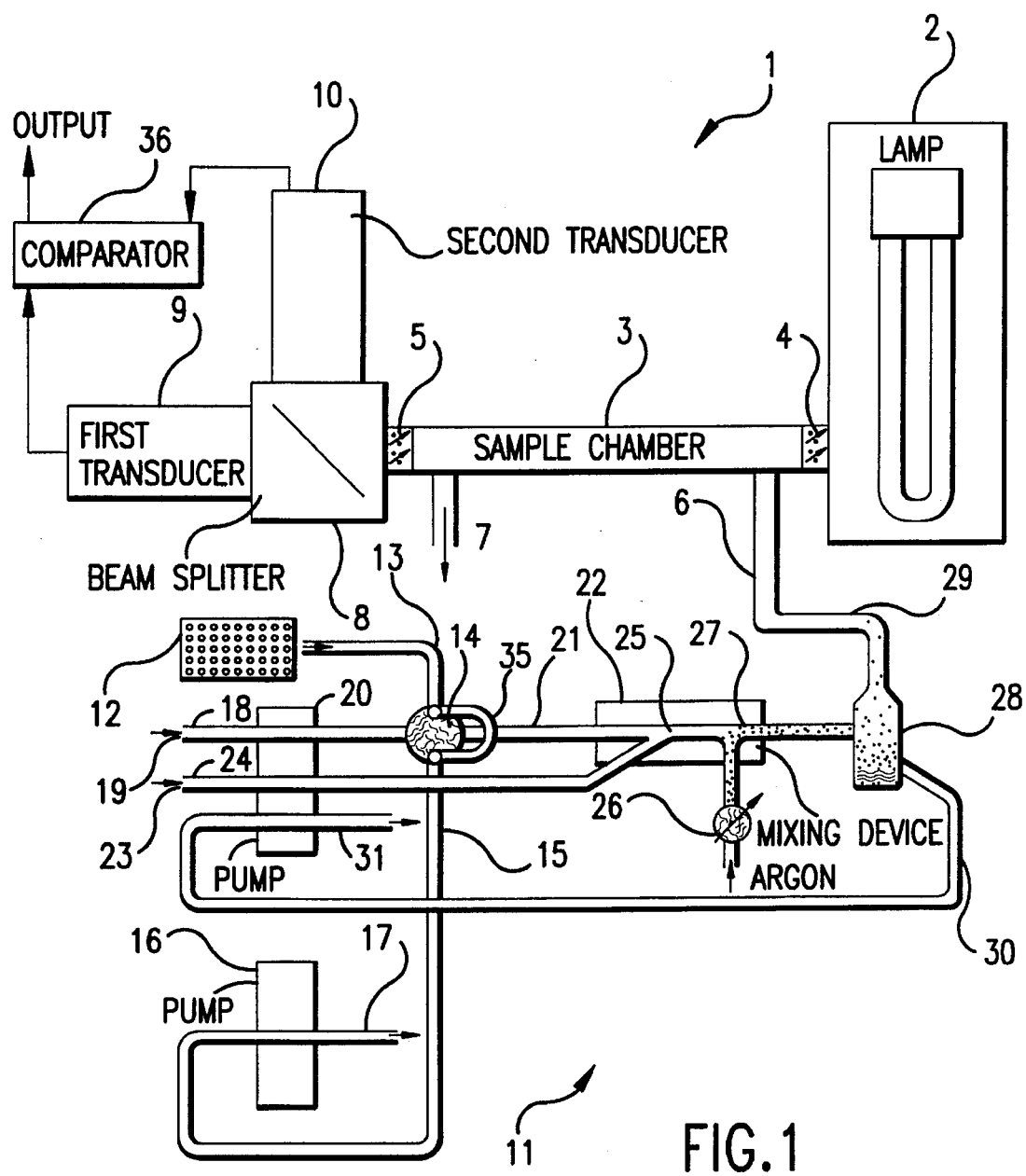
FIG. 1 is a diagrammatic illustration of a preferred embodiment of an atomic absorption spectrometer designed in accordance with the invention with a supply device for introducing the sample into the sample accommodating chamber.

In FIG. 1, numeral 1 designates the atomic absorption spectrometer in a general way. Numeral 2 designates a radiation source which produces radiation of the emission lines 184.9 and 253.7 of mercury. Such a radiation source may, for instance, be comprised by a mercury low-pressure discharge lamp. The radiation produced thereby is radiated via a window (not shown in more detail) through a sample accommodating chamber 3. In the present embodiment the sample accommodating chamber is formed by a cylindrical cell which is closed by quartz plates 4 and 5 at its opposite ends. The quartz plates may for instance have a thickness of 1 mm. The cell can be closed after the sample has been filled in, and heating devices may for instance be provided for converting the mercury contained in the sample into its atomic state. The mercury sample is preferably introduced already in its atomic state in a carrier gas flow into the cell or even passed via an inlet 6 and an outlet 7 on the cell through the latter during measurement.

In the direction of the longitudinal axis of the cell, a beam splitter 8 is arranged at the end of cell 3 which is opposite to the radiation source 2. The beam splitter 8 consists of a quartz disk which has a thickness of about 1 mm. The quartz disk is positioned at an angle of 45° relative to the longitudinal axis of the cell. Part of the radiation leaving the cell can thus pass through the beam splitter while another part is deflected by the beam splitter by 90° from said direction by way of reflection. A first electro-optical transducer 9 is arranged along the longitudinal axis of the cell behind the beam splitter while a second electro-optical transducer 10 is arranged in a direction turned by 90° in comparison therewith in such a manner that it absorbs radiation reflected by beam splitter 8.

By contrast, only the radiation passing through the beam splitter impinges on the first electro-optical transducer 9. The electro-optical transducers may be of the type which is preferably responsive to one of the two emission lines 184.9 and 253.7, respectively. A CsI photocathode for measuring the intensity of the line 184.9 nm and a CsTe photocathode for measuring the emission line 253.7 have turned out to be especially advantageous.

The sample introducing device, which is generally designated by 11, comprises a sample storing means and a sample removing device 12. The sample removing device communicates via a line 13 with a sample proportioning valve 14, which may be a so-called FIA valve. The sample proportioning valve 14 communicates via a line 15 with a first pump 16. Waste liquid can be discharged into a container (not shown) at end 17 of line 15.

Furthermore, there is provided a line 18 via which carrier liquid can be supplied at end 19 thereof. Line 18 communicates via a second pump 20 with another connection of the sample proportioning valve 14. Line 18 can be connected in a corresponding position of the sample proportioning valve 14 with a line 21 that ends in a mixing device 22.

A reducing agent can be introduced into the mixing device 22 past valve 14 via end 23 of another line 24 and the second pump 20. Downstream of the connection point 25, at which the carrier liquid and the reducing agent are combined, the supply of a neutral gas or noble gas, such as argon, into line 27 is controlled via a pressure control device 26. Line 27 terminates in a gas/liquid separation device 28. Gas can directly be introduced into the cell via line 29 which is connected to the gas/liquid separation device on the one hand and inlet 6 at cell 3 on the other hand. Waste liquid can be discharged from the gas/liquid separation device via a line 30 and the second pump 20 at the end 31 of line 30 into a container (not shown).

Figure 2:
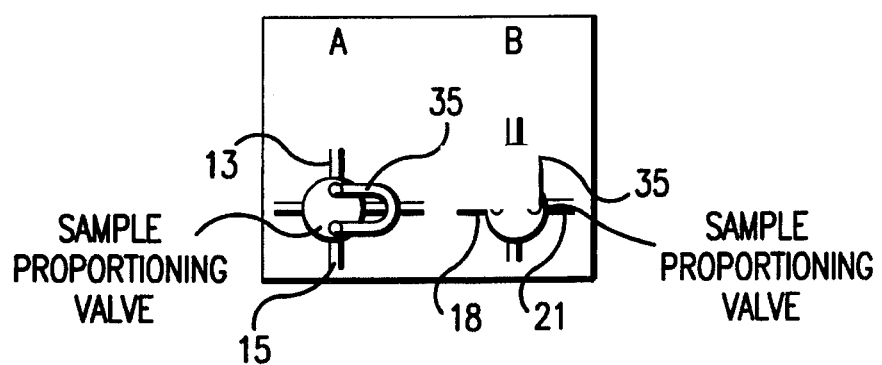
FIG. 2 is an illustration of two different functional positions of the FIA valve shown in FIG. 1.

FIG. 2 illustrates the two possible positions A and B of the sample proportioning valve 14. Line 13 is connected to line 15 via metering loop 35 in position A. Line 18 is connected to line 21 via metering loop 35 in position B.

The sample supply device 11 operates as follows:

In position A of the sample proportioning valve 14, which is shown in FIG. 2, a sample liquid flow is transported from the sampling device 12 via line 13, sample proportioning loop 35 of the sample proportioning valve 14, line 15 and the first pump 16 towards end 17 of line 15. As soon as the sample proportioning loop 35 has entirely been filled with the sample, the sample proportioning valve 35 is moved into position B, which is illustrated in FIG. 2. A predetermined amount of sample is first sealed in the sample proportioning loop 35. The amount of sample desired for the assay can be determined by selecting different sample proportioning loops 35 with which sample amounts of e.g. 0.5 or 1 ml or less or more can be proportioned.

As soon as sample proportioning valve 14 has been moved into position B, carrier liquid is pumped through the sample proportioning loop 35 from line 18 with the aid of the second pump 20, and the sample is thus supplied into the sample mixing device 22. Reducing agent is continuously supplied via line 24 at the mixing point 25 into said sample mixing device 22. The mercury in the sample is reduced by the reducing agent into its atomic state. A carrier gas flow with a specific flow rate is produced by supplying, e.g., argon gas at a predetermined pressure with the aid of the pressure control device 26. If this carrier gas flow still includes liquid, the liquid is separated in the gas/liquid separation device. While the liquid amount is transported via line 30 and the second pump to the outlet end 31 as waste liquid, the carrier gas flow which contains the mercury sample in the atomic state flows via line 29 and inlet 6 into cell 3 and at the end thereof through outlet 7 out of the cell.

In one embodiment the cell had an inner diameter $r=0.6$ cm and a length $L=20$ cm. This gives a volume $V=23$ cm$^3$. The flow of argon gas was $F=100$ ml/60 s. Hence, the flow rate was so great that within a time of $F\times V=13.8$ s the whole volume of the cell was replaced once. The measurement time was preferably chosen such that it was at least five times the period of change for the replacement of the volume of the cell.

The atomic absorption spectrometer is calibrated such that the light intensity $I_0$ is measured both on the first and second photocathodes 9 and 10, respectively, while cell 3 is irradiated with radiation from radiation source 2 when only carrier gas first flows through the cell at a predetermined rate of e.g. 100 ml/min without addition of a sample by valve 14. The measurement values of the light intensity $I_0$ that are normally different for the two cathodes represent the unattenuated radiation of the background radiator Hg lamp 2. Then a predetermined amount of sample is successively added to the gas flow in accordance with the capacity of the sample proportioning loop 35 with respectively different concentrations of mercury. During passage of the sample through the cell there is an increased absorption of the radiation of both emission lines 184.9 and 253.7, respectively. If the ratio of the previously measured reference intensity $I_0$ and of the intensity I measured with the sample is arithmetically formed for the light intensities I measured during passage of each sample past the two cathodes 9 and 10, and if the logarithm is formed therefrom, one obtains the mathematical value of the extinction $E=\log I_0/I$. The curve of the extinction values determined thereby during passage of a sample through the cell has about the appearance shown in FIG. 3. The time during measurement is plotted in seconds on the abscissa while the extinction values formed thereby are plotted on the ordinate. Signals with about the same extinction first appear on the two photocathodes 9 and 10 during passage of the pure carrier gas within the period of about 2 to 17 seconds. The carrier flow which transports the sample flows through the cell from this time onwards and produces a curve with a considerably rising extinction on the photocathode which is substantially adjusted to the emission line 185 nm whereas at the same time the other photocathode adjusted to the emission line 254 nm shows an only negligibly increased signal with increased extinction values. As becomes apparent from the curve, the sample passes through the cell approximately during a period of from 13 to 14 seconds. To determine the extinction values to be used for calibrating the spectrometer, either the method for determining the extinction value in the peak of each absorption curve may be used or a method in which the extinction value is determined by integration of the area positioned below the peak curve. If one chooses the determination of the extinction value according to the peak of the respective curve, this will yield, for instance, an extinction value of about 0.03 on the photocathode which is substantially responsive to the emission line 185 nm while the extinction value for the photocathode substantially responsive to the emission wavelength 254 nm is at about 0.003. Hence, both extinction values virtually differ by a factor 10.

The extinction values determined with the standard samples are shown in FIG. 4 in two respective curves (185 nm and 254 nm) in a diagram in which the concentration of mercury is indicated on the abscissa in ng and the extinction on the ordinate. As becomes apparent, the calibration curve for 185 nm has a straight steep rise in the range of very low mercury concentrations, namely from 0.01 to 1 ng. In comparison therewith, the sensitivity of the photocathode which is responsive to the emission line 254 nm is smaller by virtually one power of ten. This curve, however, has a straight steep rise in the range of about 0.5 to more than 100 ng. These different properties of the respective photocathodes are advantageously used by the invention such that the mercury concentration, i.e. the amount of mercury contained in the predetermined sample volume, is determined such that the measurement values of the photocathode (185 nm) are used for the determination of the mercury amount when the extinction values measured on said photocathode are within an extinction range of from 0.001 to 0.1 in the calibration diagram shown in FIG. 4, while the amount of mercury is determined by way of the extinction values measured by the photocathode (254 nm) when the extinction values measured there are approximately in the range between 0.01 and 1. Such an automatic switching between the respective measurement ranges can easily be implemented electronically, e.g., with the aid of a comparator 36. A considerably enlarged dynamic measuring range can be implemented in this way, i.e., the concentration measuring range which can be achieved in this way covers a total range of about four orders of magnitude, namely, for instance, 0.01 to 100 ng mercury.

The enhanced measuring capacity shall once again be explained with reference to the two following examples, of which example 1 relates to the analysis of rain water with added mercury and the second example to an analysis of mercury in urine.

| Sample Volume: 0.5 ml | Extinction | |
| --- | --- | --- |
| Reducing Agent | 0.2% NaBH$_4$ in 0.05% NaOH | 1% SnCl$_2$ in 0.3% HCl |
| Carrier Liquid | 3% HCl, superpure | 3% HCL, superpure |
| Standard: | | |
| 30 ng/l | 0.00148 | 0.0019 |
| 50 ng/l | 0.00523 | 0.0041 |
| 100 ng/l | 0.01076 | — |
| rain water | 0.00552 | 0.0037 |
| Hg Content/pg | 28 | 23 |

A sample volume of 0.5 ml was respectively used in Example 1. 0.2% NaBH$_4$ in 0.05% NaOH was used as a reducing agent and 3% HCl superpure was used as carrier liquid whereas in a second different run 1% SnCl$_2$ in 0.3% HCl was used as a reducing agent and 3% HCl superpure as carrier liquid. The extinctions for three different standards, namely 30 ng/l, 50 ng/l and 100 ng/l were then determined. Thereupon a rain water sample was determined according to both methods with an extinction value of 0.0052 in one case and 0.0037 in another case. A Hg content of 28 picograms followed in the first case from the two measurements and of 23 picograms in the other case. 25 picograms were measured in corresponding assays with the same sample in the Lake Constance Water Supply Works of Ueberlingen.

EXAMPLE 2

Analysis of Hg in urine

Reducing Agent: 0.2% NaBH$_4$+0.05% NaOH

Carrier Liquid: 3% HCl superpure

Sample Volume: 1 ml

| | Hg Content μg/l | |
| --- | --- | --- |
| Samples | Measured | Nominal |
| Lanonorm 1 | 10.0 ± 0.5 | 11.8 ± 2 |
| Bio-RAD1 | 8.1 ± 0.5 | 5.2 ± 2 |
| Humanurin | 0.3 ± 0.03 | — |

We claim:

1. An atomic absorption spectrometer for measuring mercury concentration in a sample comprising:

means for producing predetermined emission lines of the mercury at the same time, a sample accommodating chamber which can be irradiated with radiation of the emission lines, two means for measuring the extinction of the radiation passing through the sample accommodating chamber, each means for measuring the extinction having an electro-optical transducer which is responsive with a different sensitivity to radiation of the emission lines respectively, the transducers being arranged so that radiation passing through the sample accommodating chamber simultaneously impinges on said two electro-optical transducers and each extinction measuring means having a preselected extinction value range, and means for switching between respective measurement ranges of said two extinction measuring means to determine the mercury concentration.

2. An atomic absorption spectrometer according to claim 1, further comprising a beam splitter between the sample accommodating chamber and the electro-optical transducers.

3. An atomic absorption spectrometer according to claim 2, wherein said beam splitter consists of a quartz plate.

4. An atomic absorption spectrometer according to claim 3, wherein said quartz plate has a thickness of 1 mm.

5. An atomic absorption spectrometer according to claim 2, wherein said beam splitter is arranged at an angle of 45° relative to an axis of radiation exiting from said sample chamber, wherein one of said electro-optical transducers is arranged along said axis, and wherein the other electro-optical transducer is arranged at an angle of 90° relative to the axis.

6. An atomic absorption spectrometer according to claim 1 further comprising mean for transferring mercury from a solution into a carrier gas, said means for transferring being connected to said accommodating chamber.

7. An atomic absorption spectrometer according to claim 1, wherein said means for producing predetermined emission lines of the mercury comprises a Hg low-pressure discharge lamp.

8. An atomic absorption spectrometer according to claim 1, wherein said extinction value ranges of said two means for measuring the extinction extend over four orders of magnitude.

9. An atomic absorption spectrometer according to claim 1, further comprising reducing means for reducing mercury.

10. An atomic absorption spectrometer according to claim 9, wherein said reducing means includes a flow-injection system.

11. An atomic absorption spectrometer according to claim 1, wherein the means for producing predetermined emission lines produces lines at 184.9 nm and 253.7 nm.

12. An atomic absorption spectrometer according to claim 11, wherein a first of said electro-optical transducers includes a CsTe photocathode which is predominantly responsive to radiation of the emission line 253.7 rim and a second of said electro-optical transducers includes a CsI photocathode which is substantially responsive to radiation of the emission line 184.9 nm.

\* \* \* \* \*